United States Patent
Kim et al.

(10) Patent No.: US 9,880,109 B2
(45) Date of Patent: Jan. 30, 2018

(54) VISION INSPECTION APPARATUS AND METHOD OF DETECTING MURA THEREOF

(71) Applicants: Samsung Display Co., Ltd., Yongin, Gyeonggi-Do (KR); KOREA UNIVERSITY RESEARCH AND BUSINESS FOUNDATION, Seoul (KR)

(72) Inventors: Se-Yun Kim, Daegu (KR); Sung-Jea Ko, Seoul (KR); Hoi-Sik Moon, Asan-si (KR)

(73) Assignees: Samsung Display Co., Ltd., Yongin-si (KR); Korea University Research and Business Foundation, Seoul (KR)

( * ) Notice: Subject to any disclaimer, the term of this patent is extended or adjusted under 35 U.S.C. 154(b) by 264 days.

(21) Appl. No.: 14/601,448

(22) Filed: Jan. 21, 2015

(65) Prior Publication Data

US 2016/0012759 A1   Jan. 14, 2016

(30) Foreign Application Priority Data

Jul. 9, 2014   (KR) .................. 10-2014-0086093

(51) Int. Cl.
   *G01N 21/956*   (2006.01)
   *G01N 21/95*   (2006.01)

(52) U.S. Cl.
   CPC ... *G01N 21/956* (2013.01); *G01N 2021/9513* (2013.01)

(58) Field of Classification Search
   None
   See application file for complete search history.

(56) References Cited

U.S. PATENT DOCUMENTS

| | | | |
|---|---|---|---|
| 2010/0008591 A1* | 1/2010 | Su | G09G 3/2092 382/232 |
| 2011/0227964 A1* | 9/2011 | Chaji | G09G 3/006 345/690 |
| 2014/0168451 A1* | 6/2014 | Lee | G09G 3/006 348/189 |

FOREIGN PATENT DOCUMENTS

| | | |
|---|---|---|
| JP | 2004-212311 | 7/2004 |
| KR | 1020050104855 A | 11/2005 |
| KR | 1020080060469 A | 7/2008 |
| KR | 1020120010009 A | 2/2012 |
| KR | 1020130090211 A | 8/2013 |

* cited by examiner

*Primary Examiner* — Christopher Kohlman

(74) *Attorney, Agent, or Firm* — H.C. Park & Associates, PLC

(57) ABSTRACT

A display apparatus includes a background image estimator configured to restructure a plurality of pixel signals of a panel image corresponding to a plurality of pixels arranged in an (n×m) matrix array into a row dataset and a column dataset and generate a row background image and a column background image with a Mura defect removed from the panel image using the row dataset and the column dataset through a Principal Component Analysis (PCA), a Mura image generator configured to generate a row binary image and a column binary image including a background and the Mura defect using differences between the panel image and the row background image and between the panel image and the column background image.

9 Claims, 10 Drawing Sheets

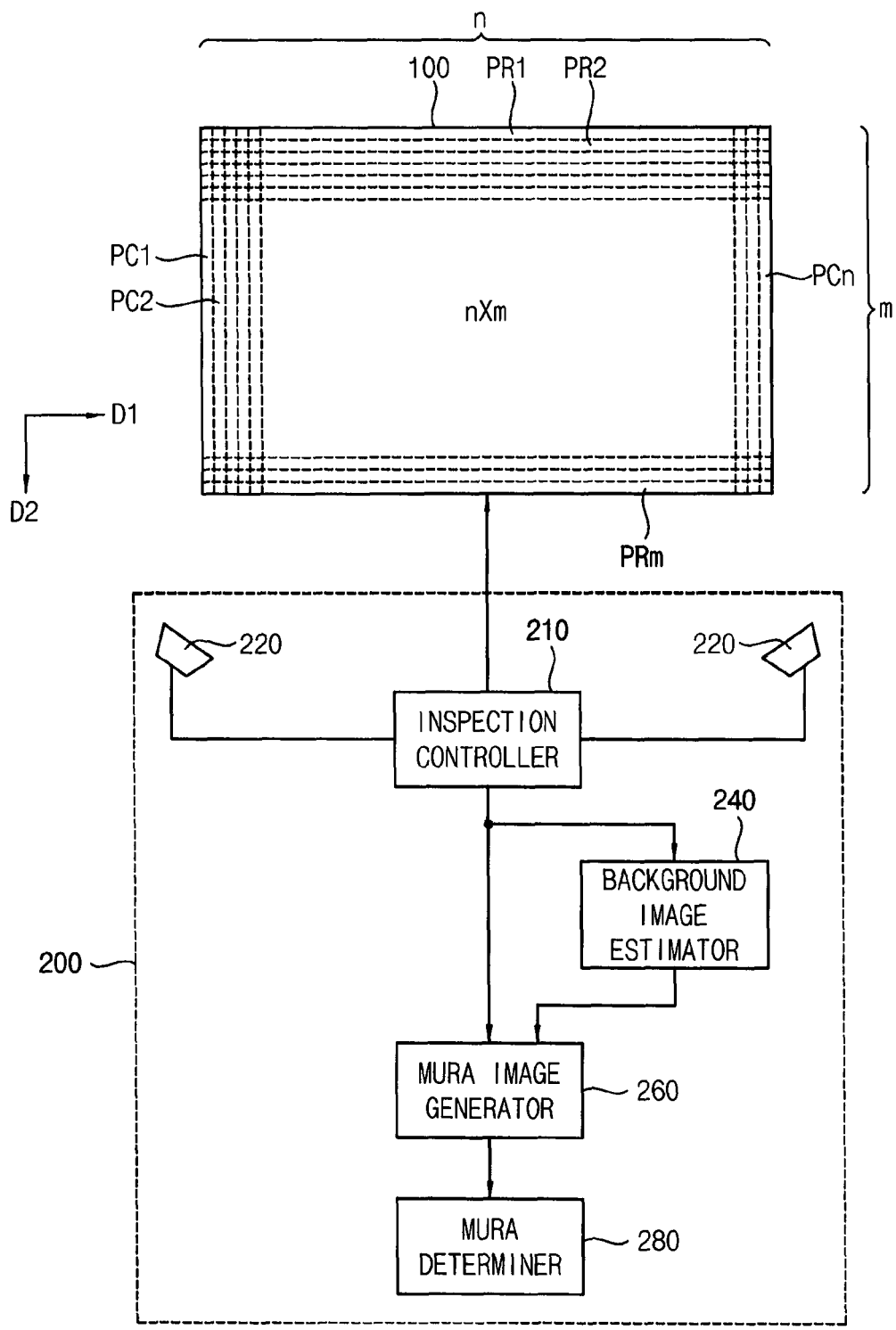

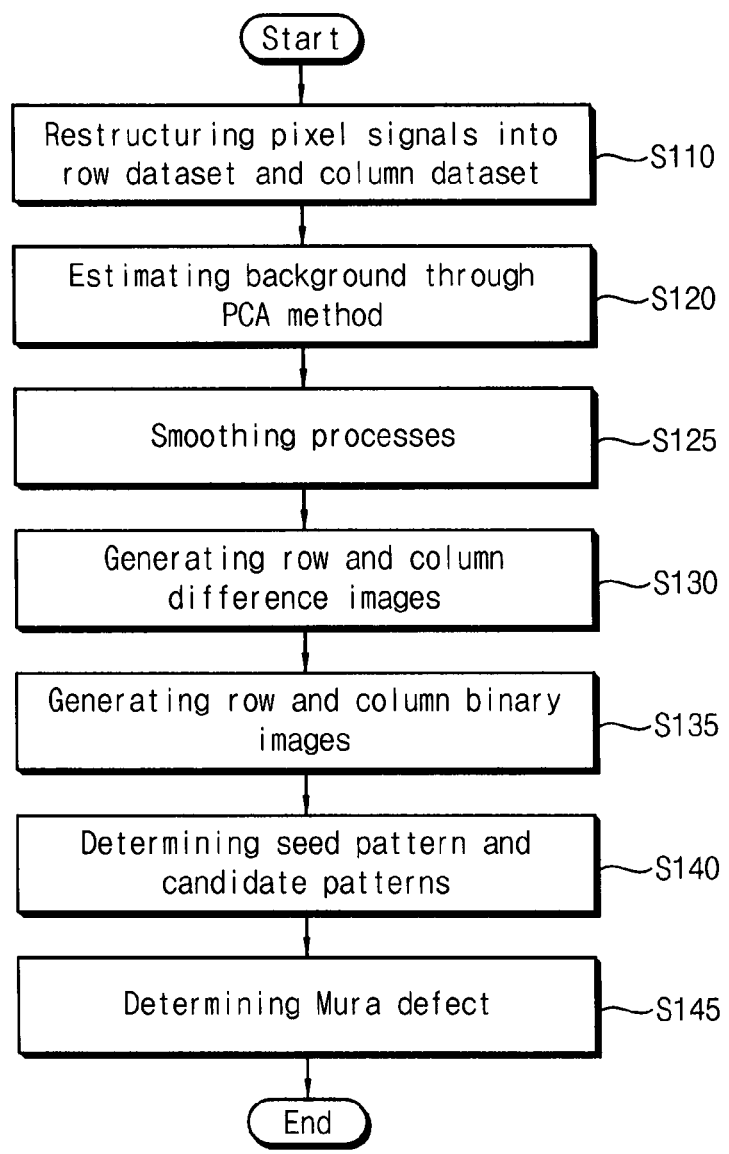

SEED EXPANSION

MURA DETECTION RESULT

VISION INSPECTION APPARATUS AND METHOD OF DETECTING MURA THEREOF

This application claims priority from and all the benefits under 35 U.S.C. §119 of Korean Patent Application No. 10-2014-0086093, filed on Jul. 9, 2014 in the Korean Intellectual Property Office, which is hereby incorporated by reference for all purposes as if fully set forth herein.

BACKGROUND OF THE INVENTION

Field of the Invention

Exemplary embodiments of the inventive concept relate to a vision inspection apparatus and a method of detecting a Mura defect. More particularly, example embodiments of the inventive concept relate to a vision inspection apparatus for automatically and accurately detecting a Mura defect and a method of detecting the Mura defect.

Description of the Related Art

In general, a liquid crystal (LC) display panel includes a lower substrate, an upper substrate opposite to the lower substrate and an LC layer disposed between the upper substrate and the lower substrate. The lower substrate includes a pixel area defining a pixel and a peripheral area receiving a driving signal which is to be applied to the pixel.

A data line, a gate line and a pixel electrode are disposed in the pixel area. The data line extends in a first direction, the gate line extends in a second direction crossing the first direction and the pixel electrode is connected to the data line and the gate line. A first driving chip pad and a second driving chip pad are disposed in the peripheral area. The first driving chip pad receives a data signal and the second driving chip pad receives a gate signal.

The LC panel, with the LC layer disposed between the upper substrate and the lower substrate, is tested through a visual test process which tests electrical and optical operations of the LC panel. In general, the visual test process includes testing various kinds of Mura defects (e.g. spot and line Mura defects, etc.) by a tester's eyes and removing the Mura defects using a Mura defect removal algorithm based on a test result obtained by the tester's eyes. As described above, the Mura defects are manually detected by the tester, increasing a test process period and test results among different testers are inconsistent. Thus, productivity may be decreased and compensation error may be increased.

SUMMARY OF THE INVENTION

Exemplary embodiments of the inventive concept provide a vision inspection apparatus for automatically and accurately detecting a Mura defect.

Exemplary embodiments of the inventive concept provide a method of detecting the Mura defect.

According to an exemplary embodiment of the inventive concept, there is provided a vision inspection apparatus. The vision inspection apparatus includes a background image estimator configured to restructure a plurality of pixel signals of a panel image corresponding to a plurality of pixels arranged in an (n×m) matrix array ('n' and 'm' are natural numbers) into a row dataset and a column dataset and generate a row background image and a column background image and in these images a Mura defect is removed from the panel image using the row dataset and the column dataset through a Principal Component Analysis (PCA), a Mura image generator configured to generate a row binary image and a column binary image and these images include a background and the Mura defect which is resulted from differences between the panel image and the row background image and between the panel image and the column background image, and a Mura defect determiner configured to determine the Mura defect, using the row binary image and the column binary image.

In an exemplary embodiment, the row dataset may be restructured into m row data of an n-dimension corresponding to m pixel rows of the panel image, the column dataset may be restructured into n column data of an m-dimension corresponding to n pixel columns of the panel image, each of m row data may include n pixel signals corresponding to n pixels in a pixel row and each of n column data may include m pixel signals corresponding to m pixels in a pixel column.

In an exemplary embodiment, the background image estimator may be configured to convert the row dataset of the n-dimension into a row dataset of a q-dimension through the PCA, to reconstruct the row dataset of the q-dimension into the row dataset of the n-dimension such that pixel signals corresponding to the row background image are generated, to convert the column dataset of the m-dimension into a column dataset of the q-dimension through the PCA, and to reconstruct the column dataset of the q-dimension into the column dataset of the m-dimension such that pixel signals corresponding to the column background image are generated (wherein 'q' is a natural number less than 'n' and 'm').

In an exemplary embodiment, the q may be 5.

In an exemplary embodiment, the Mura image generator may be configured to generate a row difference image between the panel image and the row background image, to generate a column difference image between the panel image and the column difference image, to apply a first threshold value to the pixel signals of the row difference image such that the row binary image divided into the background and the Mura defect is generated, and to apply a second threshold value to the pixel signals of the column difference image such that the column binary image divided into the background and the Mura defect is generated.

In an exemplary embodiment, the first threshold value may be calculated by an average and a standard deviation of the pixel signals corresponding to the row difference image, and the second threshold value may be calculated by an average and a standard deviation of the pixel signals corresponding to the column difference image.

In an exemplary embodiment, the Mura defect determiner may be configured to generate an intersection image including a seed pattern corresponding to a position of the Mura defect through an intersection calculation of the row binary image and the column binary image, and to generate an union image including a candidate pattern corresponding to size and shape of the Mura defect through an union calculation of the row binary image and the column binary image.

In an exemplary embodiment, the Mura defect determiner may be configured to remove a noise in the row binary image and the column binary image before the intersection calculation.

In an exemplary embodiment, the Mura defect determiner may be configured to extend the seed pattern to an outside area of the candidate pattern to determine the Mura defect.

According to an exemplary embodiment of the inventive concept, there is provided a method of detecting a Mura defect. The method includes restructuring a plurality of pixel signals of a panel image corresponding to a plurality of pixels arranged in an (n×m) matrix array ('n' and 'm' are natural numbers) into a row dataset and a column dataset, generating a row background image and a column background image which remove a Mura defect from the panel image using the row dataset and the column dataset through a Principal Component Analysis (PCA), generating a row binary image and a column binary image including a background and the Mura defect using differences between the panel image and the row background image and between the panel image and the column background image, and determining the Mura defect using the row binary image and the column binary image.

In an exemplary embodiment, the row dataset may be restructured into m row data of an n-dimension corresponding to m pixel rows of the panel image, the column dataset may be restructured into n column data of an m-dimension corresponding to n pixel columns of the panel image, each of m row data may include n pixel signals corresponding to n pixels in a pixel row and each of n column data may include m pixel signals corresponding to m pixels in a pixel column.

In an exemplary embodiment, the generating the row background image and the column background image may include converting the row dataset of the n-dimension into a row dataset of a q-dimension through the PCA, reconstructing the row dataset of the q-dimension into the row dataset of the n-dimension such that pixel signals corresponding to the row background image are generated, converting the column dataset of the m-dimension into a column dataset of the q-dimension through the PCA, and reconstructing the column dataset of the q-dimension into the column dataset of the m-dimension such that pixel signals corresponding to the column background image are generated (wherein 'q' is a natural number less than 'n' and 'm').

In an exemplary embodiment, the q may be 5.

In an exemplary embodiment, the generating the row binary image and the column binary image may includes generating a row difference image between the panel image and the row background image, generating a column difference image between the panel image and the column difference image, applying a first threshold value to the pixel signals of the row difference image such that the row binary image divided into the background and the Mura is generated, and applying a second threshold value to the pixel signals of the column difference image such that the column binary image divided into the background and the Mura defect is generated.

In an exemplary embodiment, the first threshold value may be calculated by an average and a standard deviation of the pixel signals corresponding to the row difference image, and the second threshold value may be calculated by an average and a standard deviation of the pixel signals corresponding to the column difference image.

In an exemplary embodiment, the determining the Mura defect may includes generating an intersection image including a seed pattern corresponding to a position of the Mura defect through an intersection calculation of the row binary image and the column binary image, and generating an union image including a candidate pattern corresponding to size and shape of the Mura defect through an union calculation of the row binary image and the column binary image.

In an exemplary embodiment, the determining the Mura defect further may includes removing a noise in the row binary image and the column binary image before the intersection calculation.

In an exemplary embodiment, the determining the Mura defect further may includes extending the seed pattern to an outside area of the candidate pattern to determine the Mura defect.

According to the inventive concept, the background image of panel image is estimated through the PCA method and the candidate pattern which is used to determine the size and shape of the Mura defect and the seed pattern which is used to determine the position of the Mura defect are detected such that the position, size and shape of the Mura defect may be accurately detected.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein:

FIG. 1 is a block diagram illustrating a vision inspection apparatus according to an exemplary embodiment;

FIG. 2 is a flowchart illustrating a method of detecting a Mura defect according to the vision inspection apparatus of FIG. 1;

DETAILED DESCRIPTION OF THE INVENTION

Figure 3A:
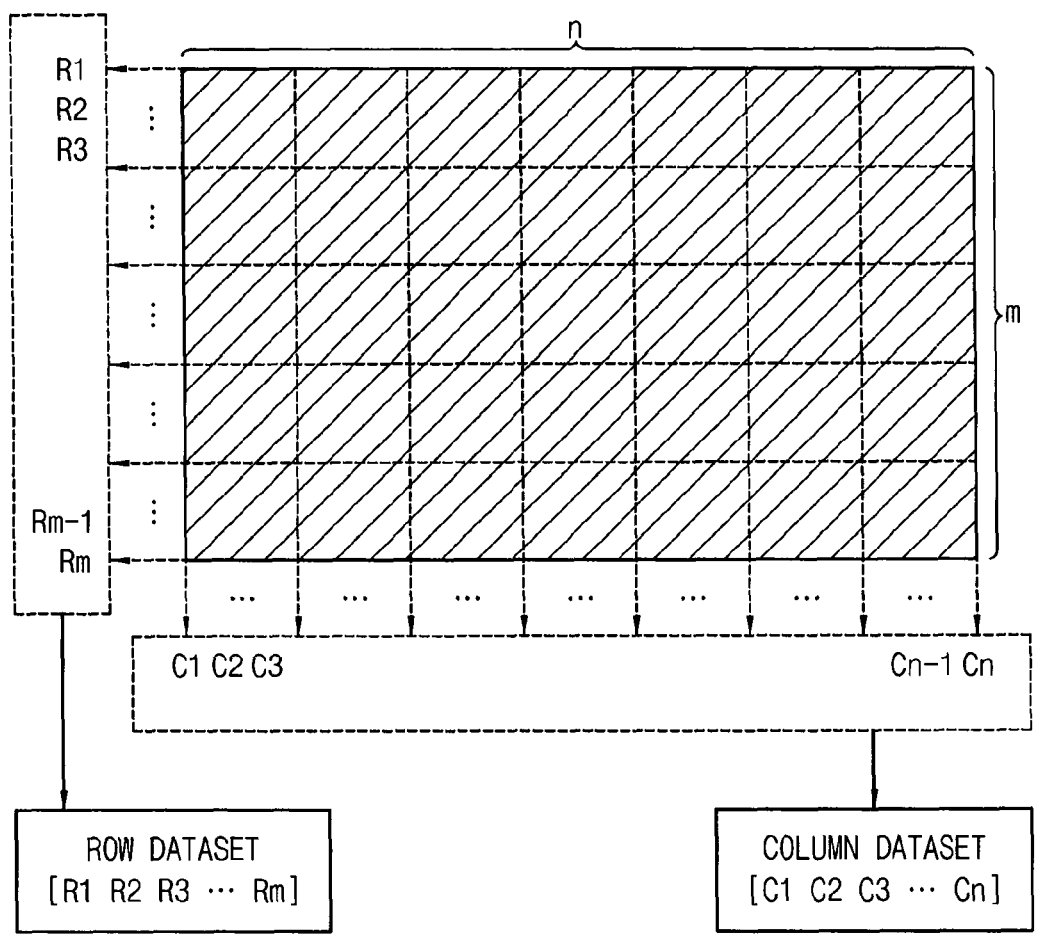
FIGS. 3A to 3C are conceptual diagrams illustrating a background image estimator of FIG. 1.

Hereinafter, the inventive concept will be explained in detail with reference to the accompanying drawings.

FIG. 1 is a block diagram illustrating a vision inspection apparatus according to an exemplary embodiment.

Referring to FIG. 1, the vision inspection apparatus 200 is configured to detect a Mura defect of a display panel 100 and to calculate a correction value compensating for the Mura defect. The Mura defect may occur by various physical factors on manufacturing processes of the display panel.

The display panel 100 may include a plurality of pixel rows PR1, PR2, . . . , PRm which are arranged in a first direction D1 and a plurality of pixel columns PC1, PC2, . . . , PCn which are arranged in a second direction D2 crossing the first direction D1. Each of the pixel rows PR1, PR2, . . . , PRm may include a plurality of pixels which are arranged in the second direction D2 and each of the pixel columns PC1, PC2, . . . , PCn may includes a plurality of pixels which are arranged in the first direction D1 (wherein 'n' and 'm' are natural numbers).

In the exemplary embodiment, the vision inspection apparatus 200 may accurately detect various Mura defect included in the display panel 100.

The vision inspection apparatus 200 according to the exemplary embodiment may include an inspection controller 210, a camera 220, a background image estimator 240, a Mura image generator 260 and a Mura defect determiner 280.

The inspection controller 210 generally controls an operation of the vision inspection apparatus 200. For example, the inspection controller 210 is configured to display sample grayscales sampled from total grayscales on the display panel 100. For example, the sample grayscales may include 0-grayscale, 16-grayscale, 24-grayscale, 32-grayscale, 64-grayscale, 96-grayscale, 128-grayscale, 192-grayscale and 255-grayscale with respect to a total grayscale number of 256, but not being limited thereto.

The camera 220 is configured to capture a panel image corresponding to a sample grayscale displayed on the display panel 100. The panel image captured from the camera 220 may include the Mura defect and a noise. The camera 220 may include a charge-coupled ("CCD") camera and a complementary metal-oxide-semiconductor ("CMOS") camera, for example.

The inspection controller 210 is configured to receive the panel image from the camera 220 and to provide the background image estimator 240 and the Mura image generator 260 with pixel signals of the panel image.

The background image estimator 240 is configured to restructure the pixel signals of a pixel row in the panel image into a row vector and to restructure the pixel signals of a pixel column in the panel image into a column vector. When the panel image has an (n×m) resolution, the panel image is restructured into a row dataset which comprises m row vectors and a column dataset which comprises n column vectors.

The background image estimator 240 is configured to estimate a background image excluding the Mura defect of the display panel 100 through a Principal Component Analysis (PCA) method. For example, the background image estimator 240 is configured to respectively apply the PCA method to the row dataset and the column dataset and to estimate a row background image and a column background image removing the Mura defect from the panel image.

In addition, the background image estimator 240 may be configured to process the row and column background images using a smoothing process such that the Mura defect similar to a background may be removed.

The Mura image generator 260 is configured to generate a difference image including the Mura defect and the noise using a difference between the panel image and the background image. For example, the Mura image generator 260 is configured to generate a row difference image using a difference between the panel image and the row background image and to generate a column difference image using a difference between the panel image and the column background image.

In addition, the Mura image generator 260 is configured to generate a row binary image corresponding to the row difference image and a column binary image corresponding to the column difference image through thresholding processes. The binary image may include the background having a black grayscale and the Mura defect having a white grayscale.

The Mura determiner 280 is configured to determine the Mura defect except for the noise using the row binary image and the column binary image. The Mura determiner 280 is configured to determine a seed pattern corresponding to a position of the Mura defect through an intersection calculation of the row binary image and the column binary image, and to determine a candidate pattern corresponding to a size and a shape of the Mura defect through an union calculation of the row binary image and the column binary image. The Mura determiner 280 is configured to determine the position, size and shape of the Mura defect based on the seed pattern and the candidate pattern and to finally detect the Mura defect.

As described above, the row background image and the column background image excluding the Mura defect is estimated using the panel image captured from the camera, the row binary image and the column binary image are generated using the panel image and the estimated row and column background images, and the Mura defect is finally detected through set calculations using the row binary image and the column binary image.

According to the exemplary embodiment, various Mura defects such as a line shape and a non-shape type may be accurately detected. In addition, the various Mura defects may be detected through signal processes of the pixel signal of the captured panel image and thus, the method of detecting the Mura defect according to the exemplary embodiment may be easily applied to various display panels including various Mura defects.

Figure 3B:
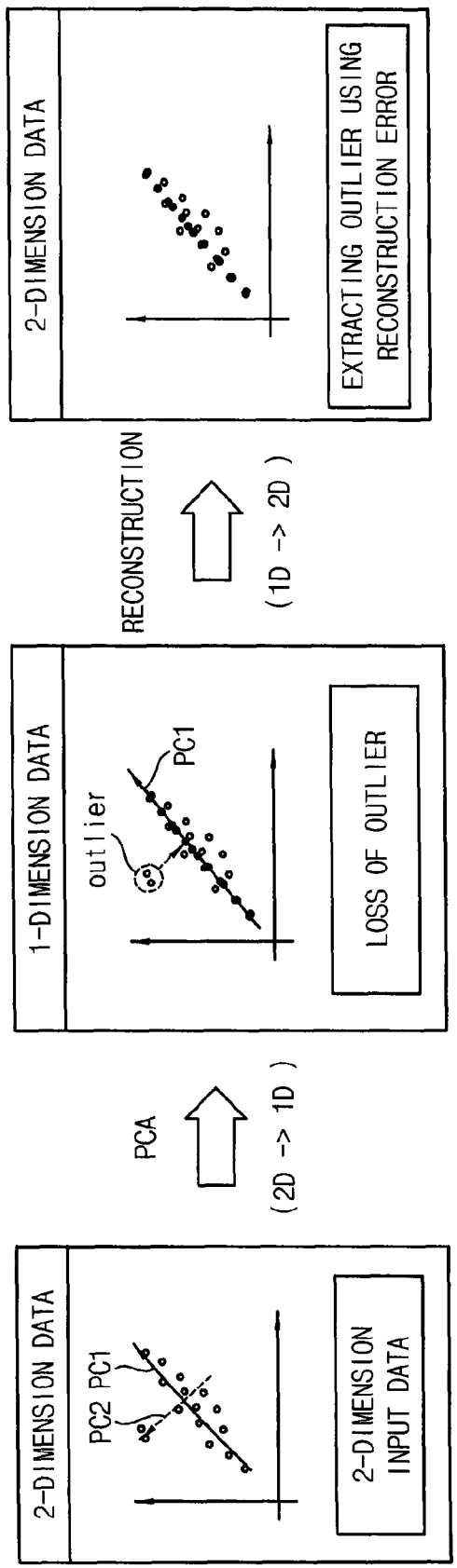
Figure 3C:
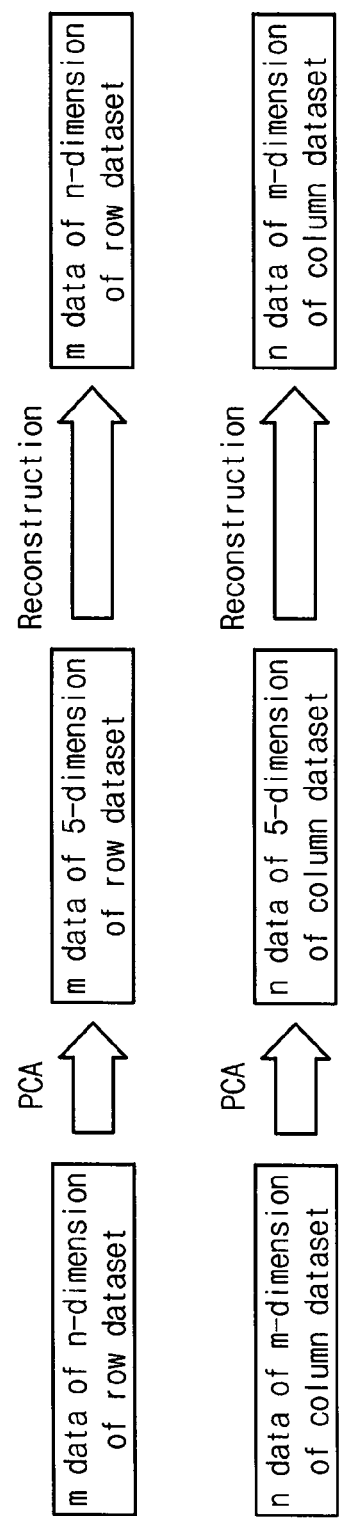
Figure 4A:
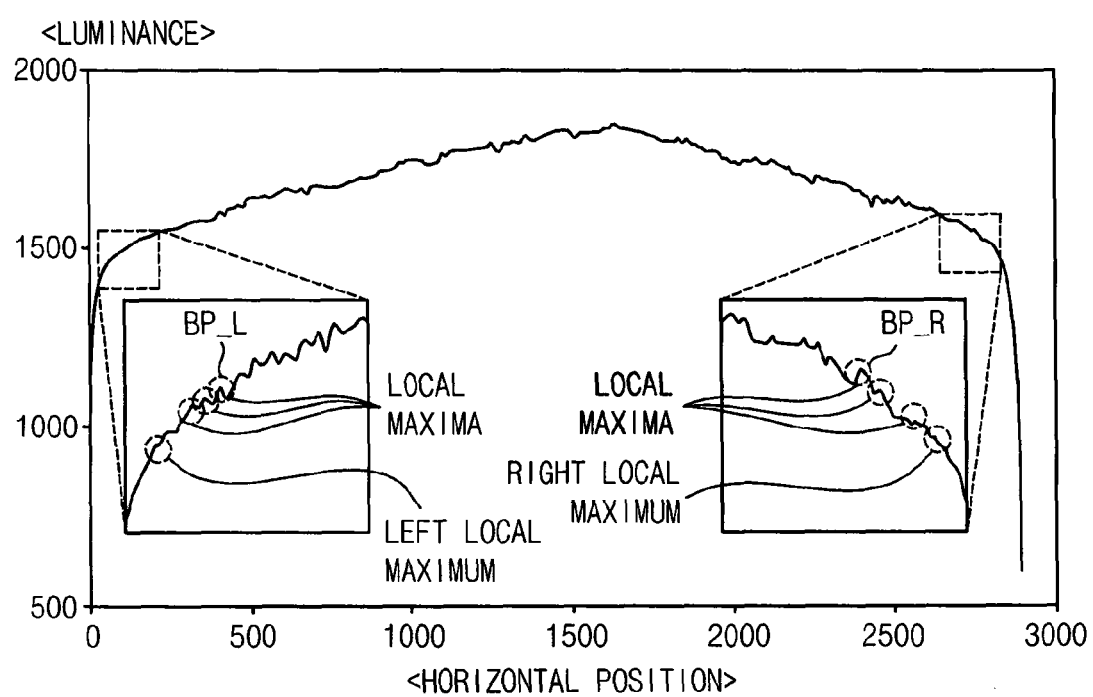
FIGS. 4A and 4B are conceptual diagrams illustrating a smoothing process according to the background image estimator of FIG. 1.
Figure 4B:
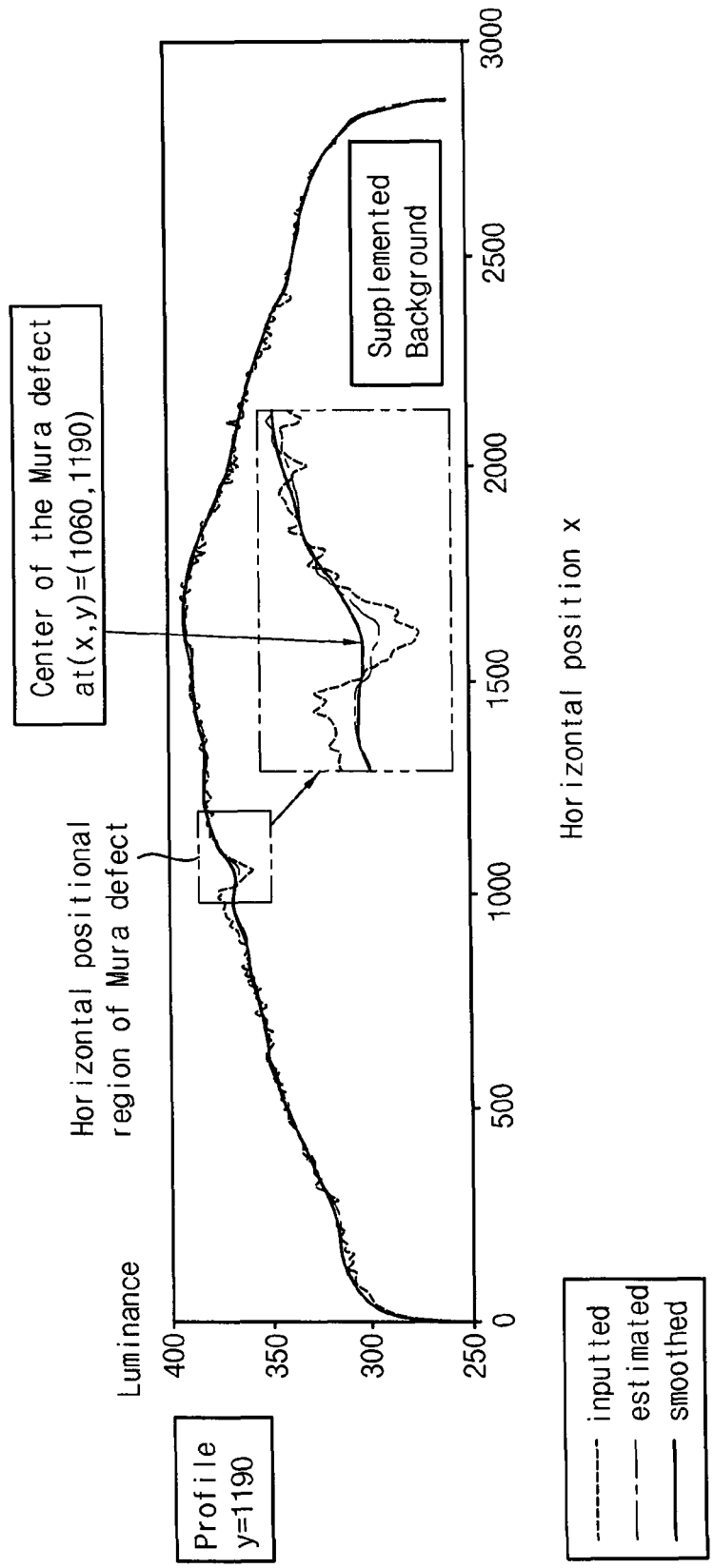
Figure 5:
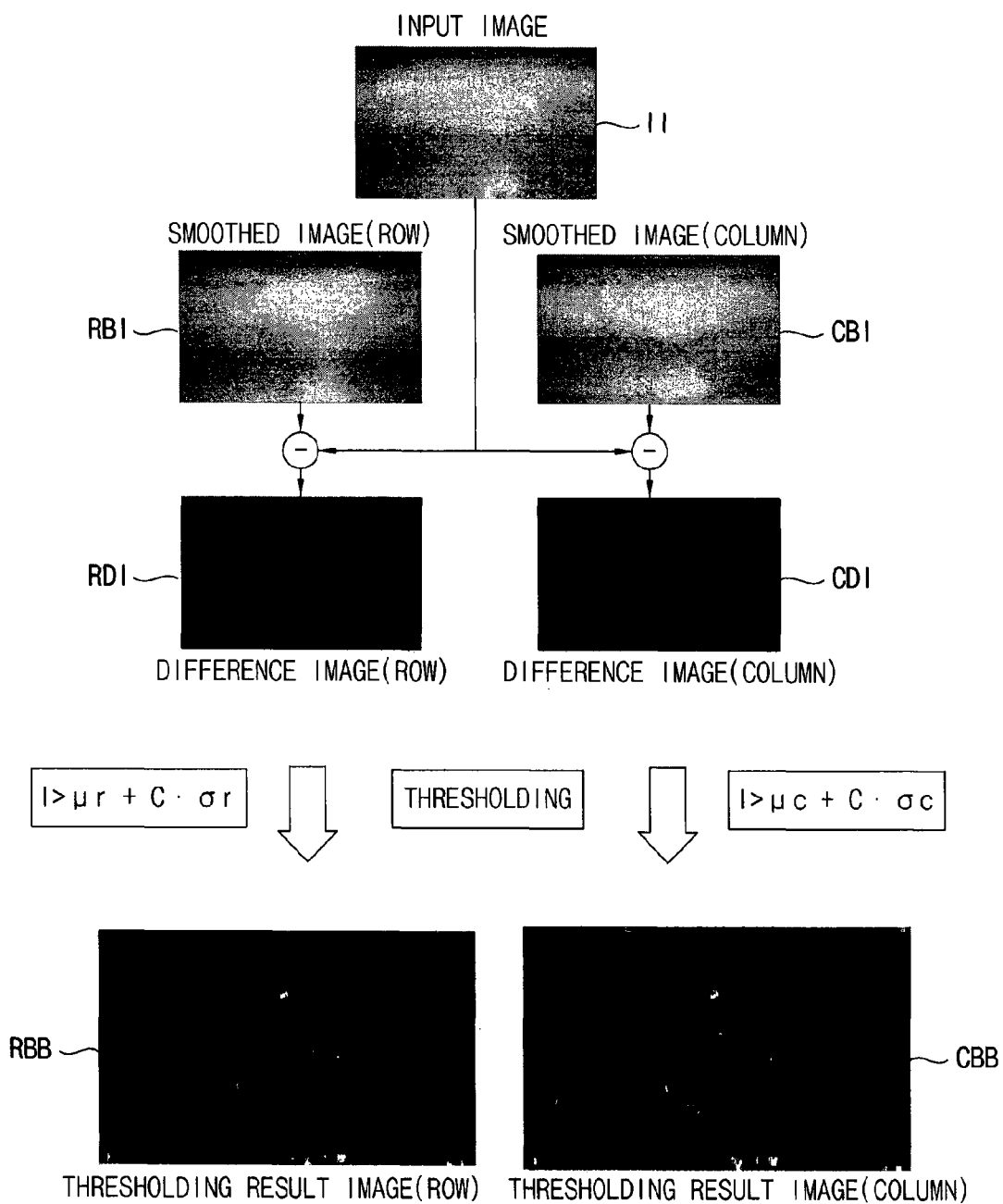
FIG. 5 is a conceptual diagram illustrating a Mura image generator of FIG. 1.
Figure 6A:
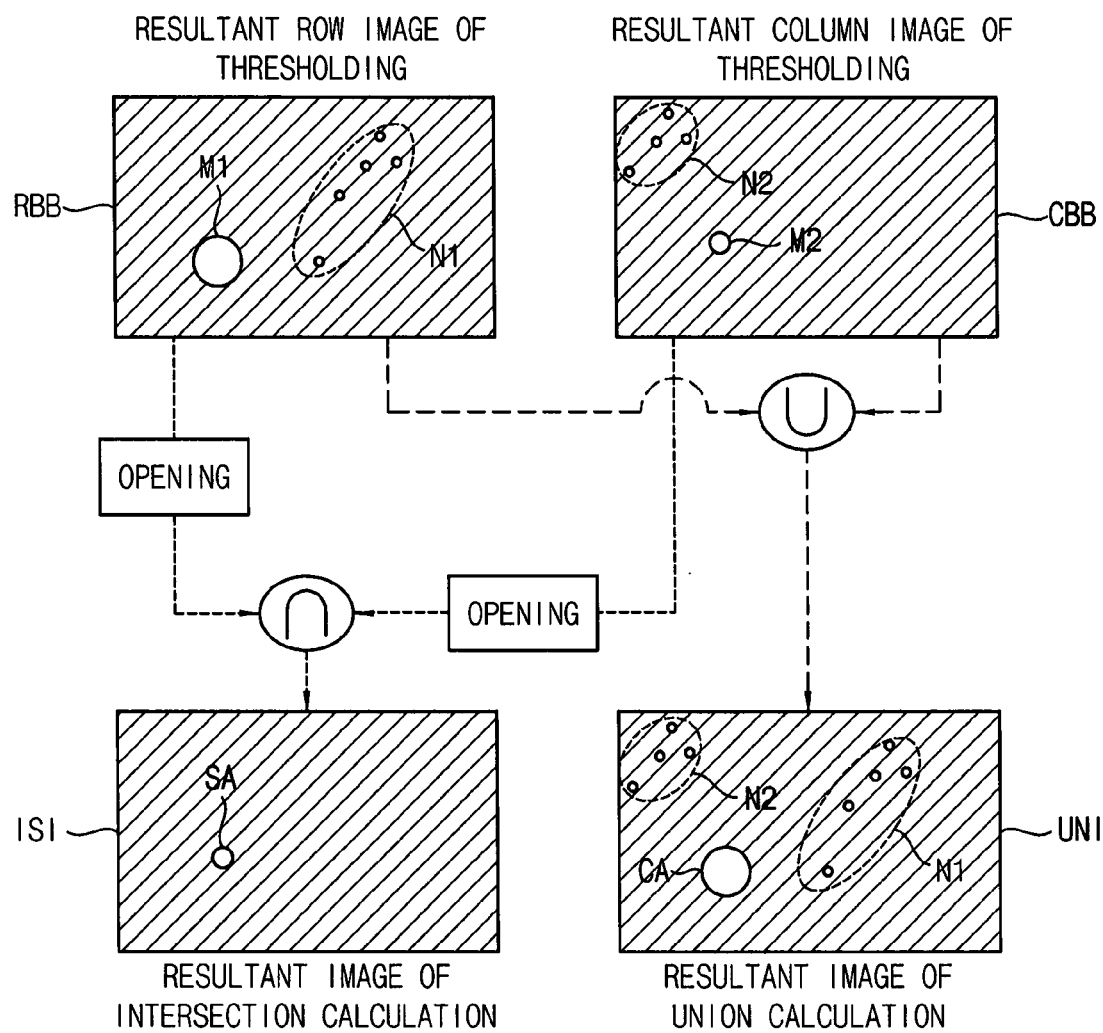
FIGS. 6A to 6C are conceptual diagrams illustrating a Mura defect determiner of FIG. 1.
Figure 6B:
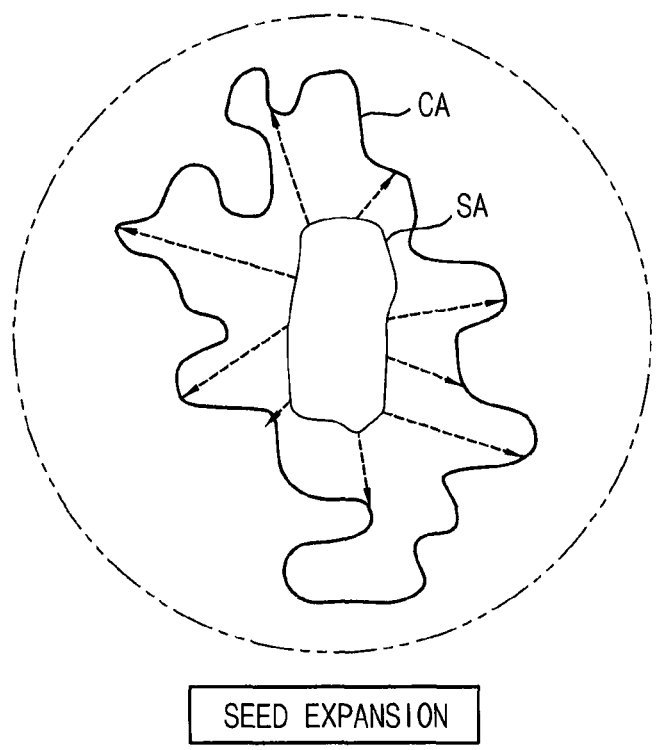
Figure 6C:
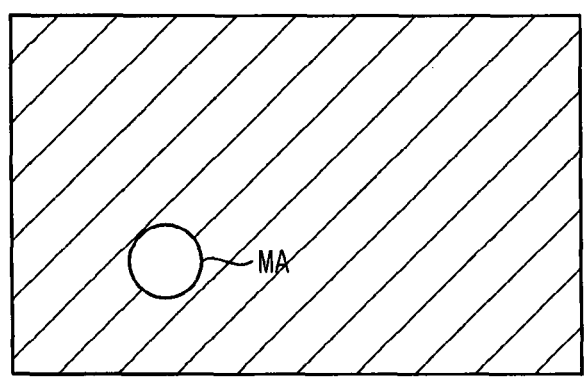

FIG. 2 is a flowchart illustrating a method of detecting a Mura defect according to the vision inspection apparatus of FIG. 1. FIGS. 3A to 3C are conceptual diagrams illustrating a background image estimator of FIG. 1. FIGS. 4A and 4B are conceptual diagrams illustrating a smoothing process according to the background image estimator of FIG. 1. FIG. 5 is a conceptual diagram illustrating a Mura image generator of FIG. 1. FIGS. 6A to 6C are conceptual diagrams illustrating a Mura determiner of FIG. 1.

Referring to FIGS. 1 and 2, the inspection controller 210 is configured to display a sample grayscale on the display panel 100.

The camera 220 is configured to capture a panel image corresponding to the sample grayscale displayed on the display panel 100 and to provide the inspection controller 210 with the panel image. The inspection controller 210 is configured to provide the background image estimator 240 with a plurality of pixel signals corresponding to the panel image.

Referring to FIG. 3A, the background image estimator 240 is configured to restructure (n×m) pixel signals of the panel image having an (n×m) resolution into m row vectors and n column vectors by applying a PAC method. Each of the row vectors is a set of n-dimension data which comprise n pixel signals corresponding to n pixels in a pixel row. Each of the column vectors is a set of m-dimension data which comprise m pixel signals corresponding to m pixels in a pixel column.

For example, a first row vector R1 is defined as n pixel signals I1,1, I2,1, I3,1, . . . , In,1 of a first pixel row PR1. A second row vector R2 is defined as n pixel signals I1,2, I2,2, I3,2, . . . , In,2 of a second pixel row PR2. As described above, an m-th row vector Rm is defined as n pixel signals I1,m, I2,m, I3,m, . . . , In,m of an m-th pixel row PRm.

A first column vector C1 is defined as m pixel signals I1,1, I1,2, I1,3, . . . , I1,m of a first pixel column PC1. A second column vector C2 is defined as m pixel signals I2,1, I2,2, I2,3, . . . , I2,m of a second pixel column PC2. As described above, an n-th column vector Cn is defined as m pixel signals In,1, In,2, In,3, . . . , In,m of an n-th pixel column PCn.

Thus, the panel image is restructured into a row dataset which comprises m row data R1, R2, R3, . . . , Rm, of an n-dimension and a column dataset which comprises n column data C1, C2, C3, . . . , Cn of an m-dimension (Step S110).

The background image estimator 240 is configured to estimate a background image of the panel image through a PCA method which analyzes dataset.

The PCA method calculates dataset of a low dimension being lower than an original dimension of input dataset.

For example, referring to 2-dimension data as shown in FIG. 3B, input dataset are the 2-dimension data and thus, the 2-dimension data include a first principal components PC1 and a second principal components PC2 perpendicular to the first principal components PC1. New dataset may be calculated using one of the first and second principal components PC1 and PC2. When the new dataset is calculated using the first principal components PC1, the new dataset may have a high reliability; however, when the new dataset is calculated using second principal components PC2, the new dataset may have a low reliability.

When the 2-dimension dataset are reduced into 1-dimension dataset using the PCA method, outlier data of the 2-dimension dataset are lost. Then, when the reduced 1-dimension dataset is reconstructed into the original 2-dimension dataset, the outlier data of the 2-dimension dataset are lost and only inlier data of the 2-dimension dataset may be obtained.

When the background image is estimated from the panel image using the PCA method, components corresponding to the Mura defect have influence less than components corresponding to the background with respect to the panel image.

Referring to FIG. 3C, the background image estimator 240 is configured to convert the row dataset which comprises m row data R1, R2, R3, . . . , Rm of the n-dimension into a row dataset which comprises m row data of a q-dimension lower than the n-dimension through the PCA, and to convert the column dataset which comprises m column data C1, C2, C3, . . . , Cn of the m-dimension into a column dataset which comprises m column data of the q-dimension through the PCA (wherein, 'q' is a natural number less than 'n' and 'm'). For example, the q is '5'.

For example, the background image estimator 240 determines an average value of the row dataset R1, R2, R3, . . . , Rm into a reference point and, to calculate a first principal components PC1 having maximum variance with respect to the reference point and a second principal components PC2 perpendicular to the first principal components PC1.

Wm,1 is a weighted value when data of an m-th row vector Rm is projected on an axis of the first principal components PC1. The weighted value Wm,1 may be calculated by a least-squared regression as following Expression 1. Wherein, v1 is a vector value with respect to the axis of the first principal components PC1.

$$W_{m,1} = \frac{(R_m - E)}{v_1}$$ Expression 1

The background image estimator 240 reconstructs the row dataset which comprises m row data of the q-dimension into the row dataset which comprises m row data of the original n-dimension and thus, new row dataset of the n-dimension corresponding to the background image expect for the Mura defect may be obtained. In addition, the background image estimator 240 reconstructs the column dataset which comprise n column data of the q-dimension into the column dataset which comprises n column data of the original m-dimension and thus, new column dataset of the m-dimension corresponding to the background image expect for the Mura defect may be obtained.

For example, the m-th row vector Rm based on the first principal components PC1 may be reconstructed into 1-dimension data R m,1'.

$$R_{m,1}' = W_{m,1} \cdot v_1 + E$$ Expression 2

Based on Expression 2, the m-th row vector Rm based on a q-th principal components PCq may be reconstructed into q-dimension data R m,q' as following Expression 3.

$$R'_{m,q} = \sum_{i=1}^{q} W_{m,i} \cdot v_1 + E$$ Expression 3

As Expressions 1 to 3 described above, the row dataset of the n-dimension are reduced into the row dataset of the q-dimension and the column dataset of the m-dimension are reduced into the column dataset of the q-dimension. And then, the row dataset of the q-dimension are reconstructed the row dataset of the n-dimension and the column dataset of the q-dimension are reconstructed the column dataset of the m-dimension. Thus, the background image except for outlier data corresponding to the Mura defect may be estimated.

As described above, the background image estimator 240 is configured to estimate the background image of the panel image using the PCA method (Step S120).

The background image estimator 240 may be configured to remove the noise in the estimated background image through smoothing processes such that the Mura defect may accurately be detected (Step S125).

Referring to a row luminance profile as shown FIG. 4A, in order to perform the smoothing processes, the display panel is divided into a central area and a peripheral area based on the peripheral area in which a luminance is sharply decreased. A boundary line is determined to divide the central area and the peripheral area.

Left and right boundary lines are determined as corresponding to left and right areas of the display panel using the row luminance profile. Upper and lower boundary lines are determined as corresponding to upper and lower areas of the display panel using a column luminance profile.

For example, first points of both end portions among local maxima based on the row luminance profile are determined into left and right boundary points BP_L and BP_R, and then the left and right boundary points BP_L and BP_R are connected to each other such that the left and right boundary lines of the display panel are determined. As described above, the upper and lower boundary lines of the display panel are determined. The central area and peripheral areas of the display panel may be divided by the boundary lines.

A 2-dimension smoothing process is performed in the central area of the display panel. A 1-dimension smoothing process is performed in the peripheral area of the display panel. As described above, the smoothing processes may be performed based on the peripheral area in which a luminance is sharply decreased.

Referring to FIG. 4B, the background image is estimated by the PCA method, and then the background image removing the noise may be obtained by the smoothing processes. Thus, the Mura defect may be accurately detected in following processes.

The background image estimator 240 provides the Mura image generator 260 with the pixel signals of the row and column background images which are finished the smoothing processes.

Referring to FIG. 5, the Mura image generator 260 is configured to generate a row difference image RDI and a column difference image CDI using the panel image II which is the input image provided from the inspection controller 210 and the row background image RBI and the column background image CBI which are finished in the smoothing processes (Step S130).

The Mura image generator 260 is configured to generate the row difference image RDI based on a difference of the panel image II and the row background image RBI, and then to generate the column difference image CDI based on a difference of the panel image II and the column background image CBI.

Then, the Mura image generator 260 is configured to calculate an average μ and a standard deviation δ of the pixel signals corresponding to the row difference image RDI, and then, to generate the row binary image RBB based on a threshold value which is calculated using the average μ and the standard deviation δ of the pixel signals corresponding to the row difference image RDI. In addition, the Mura image generator 260 is configured to calculate an average μ and a standard deviation δ of the pixel signals corresponding to the column difference image CDI, and then, is configured to generate the column binary image CBB based on a threshold value which is calculated using the average μ and the standard deviation δ of the pixel signals corresponding to the column difference image CDI (Step S135). The binary image may be calculated by the following Expression 4.

$$\text{Binary image} = \begin{cases} 1, & I > \mu + \sigma \times c \\ 0, & I \le \mu + \sigma \times c \end{cases}, c \text{ is a user-defined value} \quad \text{Expression 4}$$

The Mura image generator 260 provides the Mura determiner 280 with the row binary image RBB and the column binary image CBB.

Referring to FIG. 6A, the Mura determiner 280 is configured to generate a union image UNI through a union calculation of the row binary image RBB and the column binary image CBB.

The row binary image RBB includes a first estimated Mura M1 and a first noise N1 corresponding to the Mura defect. The column binary image CBB includes a second estimated Mura M2 and a second noise N2 corresponding to the Mura defect. Thus, the union image UNI includes a candidate pattern CA based on the union of the first and second estimated Mura M1 and M2 and the first and second noises N1 and N2. Size and shape of the candidate pattern CA may be substantially equal to those of the Mura defect. The candidate pattern CA may be used to determine the size and shape of the Mura defect.

The Mura determiner 280 is configured to generate an intersection image ISI through an intersection calculation of the row binary image RBB and the column binary image CDI.

The intersection image ISI includes a seed pattern SA based on the intersection of the first and second estimated Mura M1 and M2, and the first and second noises N1 and N2 are almost noting in the intersection image ISI. A central portion of the seed pattern SA may overlap with a central portion of the Mura defect, and a size of the of the seed pattern SA may be smaller than that of the Mura defect. Thus, the seed pattern SA may be used to determine a position of the Mura defect.

In addition, the Mura determiner 280 may be configured to perform morphological opening processes before generating the intersection image ISI such that noise components included in the row binary image RBB and the column binary image CBB may be removed.

The Mura determiner 280 is configured to determine the position and the size of the Mura defect using the union image UNI and the intersection image ISI (Step S145).

Referring to FIGS. 6B and 6C, the seed pattern SA of the intersection image ISI is located in an area corresponding to the candidate pattern CA of the union image UNI. The Mura determiner 280 extends the seed pattern SA to an outside area of the candidate pattern CA and thus determines the size and the shape of the Mura MA.

Therefore, the Mura determiner 280 determines the position, size and shape of the Mura MA and thus, the Mura defect may be finally detected.

As described above, according to exemplary embodiments, the background image of panel image is estimated through the PCA method and the candidate pattern which is used to determine the size and shape of the Mura defect and the seed pattern which is used to determine the position of the Mura detected such that the position, size and shape of the Mura may be accurately detected.

The foregoing is illustrative of the inventive concept and is not to be construed as limiting thereof. Although a few exemplary embodiments of the inventive concept have been described, those skilled in the art will readily appreciate that many modifications are possible in the exemplary embodiments without materially departing from the novel teachings and advantages of the inventive concept. Accordingly, all such modifications are intended to be included within the scope of the inventive concept as defined in the claims. In the claims, means-plus-function clauses are intended to cover the structures described herein as performing the recited function and not only structural equivalents but also equivalent structures. Therefore, it is to be understood that the foregoing is illustrative of the inventive concept and is not to be construed as limited to the specific exemplary embodiments disclosed, and that modifications to the disclosed exemplary embodiments, as well as other exemplary embodiments, are intended to be included within the scope of the appended claims. The inventive concept is defined by the following claims, with equivalents of the claims to be included therein.

What is claimed is:

1. A method of detecting a Mura defect comprising:
    restructuring a plurality of pixel signals of a panel image corresponding to a plurality of pixels arranged in an (n×m) matrix array ('n' and 'm' are natural numbers) into a row dataset and a column dataset;
    generating a row background image and a column background image with a Mura defect removed from the panel image using the row dataset and the column dataset through a Principal Component Analysis (PCA);
    generating a row binary image and a column binary image including a background and the Mura defect using differences between the panel image and the row background image and between the panel image and the column background image; and
    determining the Mura defect using the row binary image and the column binary image.

2. The method of claim 1, wherein the row dataset is restructured into m row data of an n-dimension corresponding to m pixel rows of the panel image, the column dataset is restructured into n column data of an m-dimension corresponding to n pixel columns of the panel image, each of m row data comprises n pixel signals corresponding to n pixels in a pixel row and each of n column data comprises m pixel signals corresponding to m pixels in a pixel column.

3. The method of claim 2, wherein the step of generating the row background image and the column background image comprises:
- converting the row dataset of the n-dimension into a row dataset of a q-dimension through the PCA;
- reconstructing the row dataset of the q-dimension into the row dataset of the n-dimension such that pixel signals corresponding to the row background image are generated;
- converting the column dataset of the m-dimension into a column dataset of the q-dimension through the PCA; and
- reconstructing the column dataset of the q-dimension into the column dataset of the m-dimension such that pixel signals corresponding to the column background image are generated (wherein 'q' is a natural number less than 'n' and 'm').

4. The method of claim 3, wherein the q is 5.

5. The method of claim 1, wherein the step of generating the row binary image and the column binary image comprises:
- generating a row difference image between the panel image and the row background image;
- generating a column difference image between the panel image and the column difference image;
- applying a first threshold value to the pixel signals of the row difference image such that the row binary image divided into the background and the Mura defect is generated, and
- applying a second threshold value to the pixel signals of the column difference image such that the column binary image divided into the background and the Mura defect is generated.

6. The method of claim 5, wherein the first threshold value is calculated by an average and a standard deviation of the pixel signals corresponding to the row difference image, and the second threshold value is calculated by an average and a standard deviation of the pixel signals corresponding to the column difference image.

7. The method of claim 1, wherein the step of determining the Mura defect comprises:
- generating an intersection image including a seed pattern corresponding to a position of the Mura defect through an intersection calculation of the row binary image and the column binary image; and
- generating a union image including a candidate pattern corresponding to size and shape of the Mura defect through a union calculation of the row binary image and the column binary image.

8. The method of claim 7, wherein the step of determining the Mura defect further comprises:
- removing noise in the row binary image and the column binary image before the intersection calculation.

9. The method of claim 7, wherein the step of determining the Mura defect further comprises:
- extending the seed pattern to an outside area of the candidate pattern to determine the Mura defect.

* * * * *